(12) United States Patent
Pan et al.

(10) Patent No.: US 11,766,412 B2
(45) Date of Patent: *Sep. 26, 2023

(54) METHODS OF TREATING OR ALLEVIATING ADENYLOSUCCINATELYASE (ADSL) DEFICIENCY USING SPERMIDINE OR A PHARMACEUTICALLY ACCEPTABLE SALT OF SPERMIDINE

(71) Applicant: GENEHEAL BIOTECHNOLOGY CO., LTD., Guangdong (CN)

(72) Inventors: Wuguang Pan, Guangdong (CN); Wei Zhu, Guangdong (CN)

(73) Assignee: Geneheal Biotechnology Co., Ltd., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/334,256

(22) PCT Filed: Sep. 26, 2017

(86) PCT No.: PCT/CN2017/103408
§ 371 (c)(1),
(2) Date: Mar. 18, 2019

(87) PCT Pub. No.: WO2018/059396
PCT Pub. Date: Apr. 5, 2018

(65) Prior Publication Data
US 2019/0209499 A1    Jul. 11, 2019

(30) Foreign Application Priority Data

Sep. 29, 2016  (CN) .......................... 201610865163.5

(51) Int. Cl.
| | | |
|---|---|---|
| *A61K 31/132* | (2006.01) | |
| *A61K 31/155* | (2006.01) | |
| *A61K 38/05* | (2006.01) | |
| *A61K 38/06* | (2006.01) | |
| *A61P 25/00* | (2006.01) | |
| *A61P 35/00* | (2006.01) | |
| *A61K 31/661* | (2006.01) | |
| *A61K 31/513* | (2006.01) | |

(Continued)

(52) U.S. Cl.
CPC .......... *A61K 31/155* (2013.01); *A61K 31/132* (2013.01); *A61K 31/197* (2013.01); *A61K 31/198* (2013.01); *A61K 31/33* (2013.01); *A61K 31/397* (2013.01); *A61K 31/40* (2013.01); *A61K 31/415* (2013.01); *A61K 31/4188* (2013.01); *A61K 31/43* (2013.01); *A61K 31/435* (2013.01); *A61K 31/4402* (2013.01); *A61K 31/513* (2013.01); *A61K 31/661* (2013.01); *A61K 31/675* (2013.01); *A61K 31/708* (2013.01); *A61K 31/7072* (2013.01); *A61K 31/7076* (2013.01); *A61K 38/05* (2013.01); *A61K 38/06* (2013.01); *A61K 38/063* (2013.01); *A61K 38/07* (2013.01); *A61P 3/00* (2018.01); *A61P 25/00* (2018.01); *A61P 25/08* (2018.01); *A61P 25/14* (2018.01); *A61P 35/00* (2018.01); *A61P 43/00* (2018.01); *C07D 207/12* (2013.01); *C07D 213/66* (2013.01); *C07D 213/77* (2013.01); *C07D 261/04* (2013.01); *C07D 401/04* (2013.01); *C07D 405/04* (2013.01); *C07D 473/34* (2013.01)

(58) Field of Classification Search
CPC .... A61K 31/198; A61K 2300/00; A61K 8/41; A61K 31/132; A61K 31/155; G01N 33/5008; G01N 2800/28; G01N 33/52; G01N 2500/00; G01N 33/5011; G01N 33/574; C12N 15/1137; C12N 2320/30; C12N 9/88; C12Q 1/527; C12Q 1/6886; C12Q 1/6883; C07H 21/00; C12Y 401/01021; C12Y 403/02002; C12Y 603/02006; A61P 35/00; A61P 25/00; A61P 25/28; A61P 25/08
See application file for complete search history.

(56) References Cited

U.S. PATENT DOCUMENTS

| | | | |
|---|---|---|---|
| 3,462,529 A | | 8/1969 | Forget et al. |
| 4,559,362 A | * | 12/1985 | Umezawa .............. A61K 31/13 |
| | | | 514/674 |

(Continued)

FOREIGN PATENT DOCUMENTS

| | | |
|---|---|---|
| CN | 101037423 | 9/2007 |
| CN | 101189002 | 5/2008 |

(Continued)

OTHER PUBLICATIONS

Kobayashi et al., Clin Res. 2015, abstract.*

(Continued)

*Primary Examiner* — Chang-Yu Wang
(74) *Attorney, Agent, or Firm* — Fish & Richardson P.C.

(57) ABSTRACT

Provided are compounds reducing SAICAR accumulation, and applications. On the basis of existing protein structure data and small molecule structure data, calculations and analysis are performed using software to screen and obtain compounds capable of effectively interfering with PAICS activity, reducing SAICAR synthesis, and ultimately reducing SAICAR accumulation, in order to achieve the goal of treating or improving ADSL deficiency. A better effect in the treatment or improvement of ADSL deficiency is expected from the joint use of at least two of the described compounds.

5 Claims, 3 Drawing Sheets

(51) Int. Cl.

| | |
|---|---|
| A61K 31/198 | (2006.01) |
| A61K 31/7076 | (2006.01) |
| A61K 31/675 | (2006.01) |
| A61K 31/415 | (2006.01) |
| A61K 31/4402 | (2006.01) |
| A61K 31/197 | (2006.01) |
| A61K 31/4188 | (2006.01) |
| A61K 31/708 | (2006.01) |
| C07D 213/66 | (2006.01) |
| C07D 213/77 | (2006.01) |
| C07D 405/04 | (2006.01) |
| C07D 401/04 | (2006.01) |
| A61K 31/43 | (2006.01) |
| A61P 3/00 | (2006.01) |
| C07D 261/04 | (2006.01) |
| C07D 207/12 | (2006.01) |
| A61P 25/14 | (2006.01) |
| A61K 31/33 | (2006.01) |
| C07D 473/34 | (2006.01) |
| A61K 38/07 | (2006.01) |
| A61K 31/397 | (2006.01) |
| A61K 31/7072 | (2006.01) |
| A61P 25/08 | (2006.01) |
| A61K 31/40 | (2006.01) |
| A61P 43/00 | (2006.01) |
| A61K 31/435 | (2006.01) |

(56) References Cited

U.S. PATENT DOCUMENTS

| | | | | |
|---|---|---|---|---|
| 4,952,585 | A | 8/1990 | Sunkara et al. | |
| 5,541,230 | A | 7/1996 | Basu et al. | |
| 6,235,794 | B1* | 5/2001 | Bergeron, Jr. | C07C 211/14 514/674 |
| 6,660,719 | B2* | 12/2003 | Bantia | A61K 31/00 514/43 |
| 7,056,945 | B1* | 6/2006 | Poulos | A61K 31/16 514/428 |
| 7,122,190 | B2* | 10/2006 | Bolognesi | C07K 5/0806 424/188.1 |
| 8,229,673 | B2* | 7/2012 | Palsson | G16B 5/00 702/19 |
| 8,949,032 | B2* | 2/2015 | Famili | G01N 33/5008 702/19 |
| 10,197,574 | B2* | 2/2019 | Strongin | C09K 9/02 |
| 2003/0022209 | A1* | 1/2003 | Friedman | A61K 38/1709 435/6.16 |
| 2003/0082511 | A1* | 5/2003 | Brown | G01N 33/5008 435/4 |
| 2004/0029149 | A1* | 2/2004 | Palsson | G16B 5/00 435/6.14 |
| 2004/0052820 | A1* | 3/2004 | Bolognesi | C07K 5/0806 424/208.1 |
| 2006/0147899 | A1* | 7/2006 | Famili | G01N 33/5008 435/4 |
| 2008/0176907 | A1* | 7/2008 | Silverman | A61K 31/4439 514/343 |
| 2009/0030005 | A1* | 1/2009 | Kamb | A61K 31/198 514/249 |
| 2014/0127820 | A1* | 5/2014 | Strongin | C09K 9/02 436/90 |
| 2014/0141010 | A1* | 5/2014 | Oommen | A61K 45/06 424/158.1 |
| 2015/0302141 | A1* | 10/2015 | Famili | G01N 33/5008 702/19 |
| 2016/0223558 | A1* | 8/2016 | Strongin | C09K 9/02 |
| 2016/0369281 | A1* | 12/2016 | He | C12N 15/1137 |
| 2019/0209493 | A1* | 7/2019 | Pan | A61K 8/41 |
| 2019/0209499 | A1* | 7/2019 | Pan | A61K 31/4402 |
| 2019/0298722 | A1* | 10/2019 | Ceballos-Picot | A61K 9/0053 |
| 2020/0297660 | A1* | 9/2020 | Pan | A61K 38/17 |
| 2020/0330403 | A1 | 10/2020 | Zhu et al. | |

FOREIGN PATENT DOCUMENTS

| | | | |
|---|---|---|---|
| CN | 103748091 | 4/2014 | |
| CN | 104918611 | 9/2015 | |
| CN | 105246509 | 1/2016 | |
| CN | 106399380 | 2/2017 | |
| EP | 0116693 | * 8/1984 | |
| EP | 0270349 | * 8/1988 | |
| EP | 3613416 | 2/2020 | |
| JP | 2001-172244 | 6/2001 | |
| WO | WO 1990/01036 | 2/1990 | |
| WO | WO 1997/011691 | 4/1997 | |
| WO | WO 1999/051213 | 10/1999 | |
| WO | WO 2003/037371 | 5/2003 | |
| WO | WO 2003/062255 | 7/2003 | |
| WO | WO2005/013932 | * 2/2005 | A61K 7/48 |
| WO | WO 2005/020885 | 3/2005 | |
| WO | WO 2006/099095 | 9/2006 | |
| WO | WO 2013/045826 | 4/2013 | |
| WO | WO 2014/067038 | 5/2014 | |
| WO | WO 2014/075187 | 5/2014 | |
| WO | WO2014067038 | * 5/2014 | A61K 38/17 |
| WO | WO 2014/117272 | 8/2014 | |
| WO | WO 2018/059211 | 4/2018 | |
| WO | WO 2018/059212 | 4/2018 | |
| WO | WO 2018/059395 | 4/2018 | |
| WO | WO 2018/059396 | 4/2018 | |
| WO | WO 2018/192323 | 10/2018 | |

OTHER PUBLICATIONS

WO2014067038—English translated version, published May 8, 2014.*
Meng, PhD Dissertation, Cleveland Univeristy, Nov. 2010.*
Baresova et al. Hum. Mol. Genet. 2012; 21:1534-1543.*
Bullinger et al. BMC Biochem. 2007; 8:25. doi:10.1186/1471-2091-8-25.*
Swami, MRC technology, small molecule PAICS inhibitors for metastatic breast cancer, retrieved from the website: www.biovaria.org/uploads/tx_biotechnologies/C1_Plexin_Slides_Biovaria_01.pdf.*
Kobayashi et al, abstract 3415: PAICS is the prognostic marker in colorectal cancer patients with stage III, Clin. Res. DOI: 10.1158/1538-7445.AM2015-3415, published Aug. 2015.*
Guo et al., PNAS 2004; 101:9205-9210.*
Porter et al., Can. Res. 1985; 45:2050-2057.*
Keller et al., Science. 2012; 338: 1069-1072.*
The factsheet of DB03566 from the drugbank website: www.drugbank.ca/drugs/DB03566 retrieved on Dec. 12, 2019.*
The factsheet of DB03566 from the ebi website: www.ebi.ac.uk/chebi/fr/searchld.do;266979CDB4296779F98B8B8B21B2278B?printerFriendlyView=true&locale=null&chebild=16610&viewTermLineage=null&structureView=& retrieved on Dec. 12, 2019.*
The factsheet of ADSL deficiency from the NIH/NCATS webiste: rarediseases.info.nih.gov/diseases/550/adenylosuccinase-deficiency retrieved on Dec. 13, 2019.*
Murray-Stewart et al., Biochem. J. 2016; 473:2937-2953. doi:10.1042/BCJ20160383.*
Jurecka et al., J. Inherit. Metab. Dis. 2015; 38:231-242. DOI 10.1007/s10545-014-9755-y.*
Soda, J. Exp. Clin. Cancer Res. 2011; 30:95.*
Nowotarski et a., Expert. Rev. Mol. Med. 2013; 15:e3; doi:10.1017/erm.2013.3.*
Pegg IUBMB Life, 2014; 66:8-18, DOI 10.1002/iub.1237.*
Burgess et al. J of Cell Bio. 1990, 111:2129-2138.*
Pawson et al. 2003, Science 300:445-452.*
Alaoui-Ismaili et al., Cytokine Growth Factor Rev. 2009; 20:501-507.*

(56) References Cited

OTHER PUBLICATIONS

Baresova et al. Hum. Mol. Genet. 2012; 21:1534-1543. doi:10.1093/hmg/ddr591.*
Madeo et al. ,Science, 2018; 359:eaan2788.*
Pietrocola et al., Cancer Cell, 2016; 30:147-160.*
Stark et al., J. Med. Chem., 1992; 35:4264-4269.*
Le Bot et al., Nat. Cell Biol. 2013; 15:16.*
Chadwick et al., Biorganic Med. Chern 2010:18:2586-2597.*
Noro et al. IOVS, 2015; 56:5012-5019. DOI:10.1167/iovs.15-17142.*
Tsoi et al. PLoS ONe 2016; 11:e0162217.doi:10.1371/journal.pone. 0162217.*
Balabhadrapatruni et al., The Prostate; 2017; 77:10-21.*
Devens et al., Prostate Cancer & Prostat. Diseases; 2000; 3:275-279.*
Pietrocola et al., Autophagy; 2019; 15:362-365.*
The factsheet of ADSL defiiency from the Medline Plus website: medlineplus.gov/download/genetics/condition/adenylosuccinate-lyase-deficiency.pdf retrieved on Nov. 18, 2020.*
Mouchegh et al. J. Pediatr. 2007:150:57-61.*
Perez-duenas et al. Eur. J. Pedi. Neurol.2012; 16:343-348.*
The factsheet of L-1210 cell from the ATCC website: www.atcc.org/products/ccl-219 retrieved on Jan. 18, 2022.*
The factsheet of IMC carcinoma from the Johns Hopkins website: www.hopkinsmedicine.org/breast_center/breast_cancers_other_conditions/invasive_mammary_carcinoma.html#:~:text=Cancers%20%26%20Other%20Conditions-,Invasive%20Mammary%20Carcinoma%20(IMC),common%20types%20of%20breast%20cancer retrieved on Jan. 18, 2022.*
Porter et al. Cancer Res. 1987; 47:2821-2825.*
Porter et al. Cancer Res. 1985; 45:2050-2057.*
Keller et al., Molecular Cell, 2014; 53:700-709.*
Eibmann et al. (PloS One, 2013; 8:e64873. doi:10.1371/journal. pone.0064873.*
Gaude et al. Nat. Commun. 2016; 7:13041. DOI:10.1038/ncomms13041.*
MDA-MB-231 ECACC catalog No. 92020424 retrieved from ECACC website: chrome-extension://efaidnbmnnnibpcajpcglclefindmkaj/https://www.culturecollections.org.uk/media/133182/mda-mb-231-cell-line-profile.pdf on Aug. 7, 2022.*
Casey, P. J. et al., "Inhibition of Adenylosuccinate Lyase by L-alanosyl-5-aminoi-midazole-4-carboxylic Acid Ribonucleotide (Alanosyl-AICOR)". Biochemical Pharmacology. Dec. 31, 1987 (Dec. 31, 1987), 36(5), pp. 705-709.
Casey, P. J. et al., "Metabolism of threo-β-Fluoroaspartate by $H_4$ Cells". J. Biol. Chem. Oct. 15, 1986 (Oct. 15, 1986), 261(29), pp. 13637-13642.
Jaeken J, Van den Berghe G. (Nov. 10, 1984). "An infantile autistic syndrome characterized by the presence of succinylpurines in body fluids". *Lancet* 8411:1058-1061.
Spiegel, E.K., Colman, R.F., and Patterson, D. (Jul. 12, 2006). "Adenylosuccinatelyase deficiency". Mol Genet Metab 89, 19-31.
Clamadieu, C., Cottin, X., Rousselle, C., and Claris, O. (Feb. 2008). "Adenylosuccinatelyase deficiency: an unusual cause of neonatal seizure". Arch Pediatr 15, 135-138.
Castro, M., Perez-Cerda, C., Merinero, B., Garcia, M.J., Bemar, J., Gil Nagel, A., Torres, J., Bermudez. M., Garavito, P., Marie. S., et al. (Apr. 25, 2002). "Screening for adenylosuccinatelyase deficiency: clinical, biochemical and molecular findings in four patients". Neuropediatrics 33, 186-189.
Jurecka, A., Zikanova, M., Tylki-Szymanska, A., Krijt, J., Bogdanska, A., Gradowska, W., Mullerova, K., Sykut-Cegielska, J., Kmoch. S., and Pronicka, E. (Jun. 3, 2008). "Clinical, biochemical and molecular findings in seven Polish patients with adenylosuccinatelyase deficiency". Mol Genet Metab 94, 435-442.
Ciardo, F., Salemo.C., and Curatolo, P. (May 2001). "Neurologic aspects of adenylosuccinatelyase deficiency". J Child Neurol 16, 301-308.
Gitiaux, C., Ceballos-Picot. I., Marie. S., Valayannopoulos, V., Rio, M., Verrieres, S., Benoist. J.F., Vincent, M.F., Desguerre, I., and Bahi-Buisson, N. (2009). "Misleading behavioural phenotype with adenylosuccinatelyase deficiency". Eur J Hum Genet 17, 133-136. Published online Oct. 1, 2008.
Mierzewska. H., Schmidt-Sidor, B., Jurkiewicz, E., Bogdanska, A., Kusmierska. K., and Stepien, T. (Jan. 2009). "Severe encephalopathy with brain atrophy and hypomyelination due to adenylosuccinatelyase deficiency—MRI, clinical, biochemical and neuropathological findings of Polish patients". Folia Neuropathol 47. 314-320.
Van den Bergh F, Vincent MF. Jaeken J, Van den Berghe G. (Apr. 1, 1993). "Residual adenylosuccinase activities in fibroblasts of adenylosuccinase-deficient children: parallel deficiency with adenylosuccinate and succinyl-AICAR in profoundly retarded patients and non-parallel deficiency in a mildly retarded girl", J. Inherit. Metab. Dis. 16(2) 415-424.
*Pharmaceutical Salts: Properties, Selection and Use*, P Heinrich Stahl (Editor), Camille G. Wermuth (Editor), ISBN: 3-90639-026-8, Hardcover, 388 pages, Aug. 2002.
Agarwal et al., "PAICS, a De Novo Purine Biosynthetic Enzyme, Is Overexpressed in Pancreatic Cancer and is Involved in Its Progression," Transl Oncol, 2020, 13(7):100776, 10 pages.
Agarwal et al., "PAICS, a Purine Nucleotide Metabolic Enzyme, is Involved in Tumor Growth and the Metastasis of Colorectal Cancer," Cancers (Basel), 2020, 12(4):772, 26 pages.
Chakravarthi et al., "A Role for De Novo Purine Metabolic Enzyme PAICS in Bladder Cancer Progression," Neoplasia, 2018, 20(9):894-904.
Chakravarthi et al., "Expression and Role of PAICS, a De Novo Purine Biosynthetic Gene in Prostate Cancer," Prostate, 2017, 77(1):10-21.
Chen et al., "The Non-Essentiality of Essential Genes in Yeast Provides Therapeutic Insights into a Human Disease," Genome Res, 2016, 26(10):1355-1362.
Goswami et al., "Role and regulation of coordinately expressed de novo purine biosynthetic enzymes PPAT and PAICS in lung cancer," Oncotarget, 2015, 6(27):23445-61.
Keller et al., "SAICAR Induces Protein Kinase Activity of PKM2 that is Necessary for Sustained Proliferative Signaling of Cancer Cells," Molecular Cell, 2014, 53:700-9.
Meng et al., "Knockdown of PAICS Inhibits Malignant Proliferation of Human Breast Cancer Cell Lines," Biol Res., 2018, 51(1):24, 9 pages.
Zhou et al., "Roles of highly expressed PAICS in lung adenocarcinoma," Gene, 2019, 692:1-8.
Amendola et al., "Spermine metabolism and anticancer therapy[J]," Current cancer drug targets, 2009, 9(2):118-130.
Anastasiou et al., "Pyruvate kinase M2 activators promote tetramer formation and suppress tumorigenesis." Nat Chem Biol, 2012, 8(10):839-47.
AU Office action in Australian Appln. No. 2018253689, dated Mar. 20, 2020, 4 pages.
Chen et al., "Shikonin and its analogs inhibit cancer cell givcolysis by targeting tumor pyruvate kinase-M2," Oncogene, 2011, 30(42):4297-306.
Chipperfiel et al., "Effects on the Activity of the Enzyme Phosphoribosyl-Aminoimidazole Carboxylase, 5'-Phosphate," Nucleosides and Nucleotides, 1988, 7(5-6):571-576.
Christofk et al., "The M2 splice isoform of pyruvate kinase is important for cancer metabolism and tumour growth," Nature, 2008, 452(7184):230-3.
Criss, "A Review of Polyamines and Cancer [J]," Turkish Journal of Medical Sciences, 2003, 33(4):195-205.
Eissmann et al., "A functional yeast survival screen of tumor-derived cDNA libraries designed to identify anti-apoptotic mammalian oncogenes," PLoS One, 2013, 8(5):e6487, 16 pages.
EP Office Action in European Appln. No. 17854846.7-1109, dated May 11, 2020, 9 pages.
Gerner et al., "Poly amines and cancer old molecules, new understanding [J]," Nat Rev Cancer, 2004, 4(10):781-792.
Hanahan et al., "Hallmarks of cancer: the next generation," Cell, 2011, 144(5):646-74.
Hargis et al., "Identification and Characterization of Noncovalent Interactions That Drive Binding and Specificity in DD-Peptidases and β-Lactamases," J Chem Theory Comput., 2014, 10(2):855-864.

(56) References Cited

OTHER PUBLICATIONS

Heiden, "Exploiting tumor metabolism: challenges for clinical translation," J Clin Invest, 2013, 123(9):3648-51.
Hsu et al., "Cancer cell metabolism: Warburg and beyond," Cell, 2008, 134(5):703-7.
JP Office Action in Japanese Appln. No. 2019516529, dated Jan. 30, 2020, 13 pages (with English Translation).
JP Office Action in Japanese Appln. No. 2019516529, dated May 20, 2020, 13 pages (with English Translation).
Li et al., "Octameric Structure of the Human Bifunctional Enzyme PAICS in Purine Biosynthesis," J. Mol. Biol., 2007, 366(5):1603-1614.
Mackenzie et al., "Synthesis of analogues of 5-aminoimidazole ribonucleotides and their effects as inhibitors and substrates of tire enzymes, phosphoribosylaminoimidazole carboxylase and phosphoribosylaminoimidazolesuccinocarboxamide synthetase involved in the biosynthesis of purine nucleotides de novo," Journal of the Chemical Society, Chemical Communications, 1976, 12:453-455.
Mandal et al., "Depletion of cellular poly amines, spermidine and spermline, causes a total arrest in translation and growth in mammalian cells [J]," Proceedings of the National Academy of Sciences of the United States of America, 2013, 110(6):2169-74.
Nelson et al., "Mechanism of Action of *Escherichia coli* Phosphoribosylaminoimidazolesuccinocarboxamide Synthetase†," Biochemistry, 2005, 44(2):766-774.
PCT International Preliminary Report on Patentability in International Appln. No. PCT/CN2017/103408, dated Apr. 2, 2019, 22 pages (with English Translation).
PCT International Preliminary Report on Patentability in International Appln. No. PCT/CN2018/078723, dated Oct. 22, 2019, 12 pages (with English Translation).
PCT International Search Report and Written Opinion in International Appln. No. PCT/CN2017/103408, dated Dec. 5, 2017, 30 pages (with English Translation).
PCT International Search Report and Written Opinion in International Appln. No. PCT/CN2018/078723, dated May 21, 2018, 16 pages (with English Translation).
Rial et al., "Polyamines as mediators of A.PC-dependent intestinal carcinogenesis and cancer chemoprevention [J]," Essays in biochemistry, 2009, 46(Suppl. 1 ):111-124.
Scott et al., "Reconstitution of apo-porphobilinogen deaminase: Structural changes induced by cofactor binding." FEBS Letters, 1989, 242(2):319-324.
Webb et al., "A Series of Related Nucleotide Analogues that Aids Optimization of Fluorescence Signals in Probing the Mechanism of P-Loop ATPases, Such as Actomyosin †," Biochemistry, 2004, 42(45):14463-14471.
Wolf et al., "Hexokinase 2 is a key mediator of aerobic glycolysis and promotes tumor growth in human glioblastoma multiforme," J Exp Med, 2011, 208(2):313-26.
Yihong, "Study on the Relationship between Autophagy and Viability Decrease of Eiela Cells Induced by Spermidine," China Master's Theses Full-text Database, Apr. 1, 2013, body text, p. 31, chapter 5, Conclusions.
Zhang et al., "Research Progress on Effect of Extrinsic Spennidine on Resistance of Organism," Chemistry & Bioengineering, 32(7), Jul. 25, 2015, pp. 1-4 and 21.
Zhang, "Study on Mechanism of Apoptosis Induced by Spermidine in Human Cervical Cancer Hela Cells," China Master's Theses Full-text Database, Apr. 1, 2013, body text, p. 28, chapter 5, Conclusion.
Zhang, "Study on the Apoptosis of Hela Cells Induced by Spermidine," Master Thesis, Apr. 2013, 44 pages, English Abstract.
Zikanova et al., "Preparation of 5-amino-4-imidazole-N-succinocarboxamide ribotide, 5-amino-4-imidazole-N-succinocarboxamide riboside and succinyladenosine, compounds usable in diagnosis and research of adenylosuccinate lyase deficiency," Journal of Inherited Metabolic Disease, 2005, 28(4):493-499.
AU Office Action in Australian Appln. No. 2018253671, dated Jun. 18, 2020, 4 pages.
AU Office Action in Australian Appln. No. 2018253671, dated Mar. 17, 2020, 5 pages.
Hmdb.ca [online], "Showing metabocard for SAICAR (HMDB0000797)," updated Oct. 9, 2020, [Retrieved on Jun. 17, 2021], retrieved from: URL<https://hmdb.ca/metabolites/HMDB0000797>, 10 pages.
Igarashi, Pharmacia, 1995, 31(4):373-377 (with English Abstract only).
JP Notice of Allowance in Japanese Appln. No. 2019516529, dated May 20, 2021, 5 pages (with English Translation).
JP Notice of Allowance in Japanese Appln. No. 2019551698, dated Nov. 20, 2020, 5 pages (with English Translation).
JP Office Action in Japanese Appln. No. 2019516529, dated Mar. 10, 2021, 6 pages (with English Translation).
JP Office Action in Japanese Appln. No. 2019516529, dated Sep. 7, 2020, 9 pages (with English Translation).
JP Office Action in Japanese Appln. No. 2019551698, dated Jul. 17, 2020, 10 pages (with English Translation).
KR Office Action in Korean Appln. No. 20197028417, dated Dec. 17, 2020, 15 pages (with English Translation).
Manjunath et al., "Catalytic pathway, substrate binding and stability in SAICAR synthetase: A structure and molecular dynamics study," Journal of Structural Biology, Jun. 2015, 191:22-31, http://dx.doi.org/10.1016/j.jsb.2015.06.006, 10 pages.
Marinaki et al., "Adenylosuccinate Lyase Deficiency—First British Case," Nucleosides Nucleotides & Nucleic Acids, Oct. 2004, 23(8-9):1231-1233, copy downloaded by University of Saskatchewan Library, doi: 10.1081/NCN-200027494.
Ostanin et al., "Isolation and properties of phosphoribosyl succinocarboxamideaminoimidazole synthetase from the yeast *Saccharomyces cerevisiae*," Biokhimiia (Moscow, Russia), 1989, 54(8):1265-1273 (with English Abstract).
PCT International Preliminary Report on Patentability in International Appln. No. PCT/CN2017/101062, dated Apr. 2, 2019, 21 pages (with English Translation).
PCT International Preliminary Report on Patentability in International Appln. No. PCT/CN2017/101064, dated Apr. 2, 2019, 10 pages (with English Translation).
PCT International Preliminary Report on Patentability in International Appln. No. PCT/CN2017/101066, dated Apr. 2, 2019, 14 pages (with English Translation).
PCT International Preliminary Report on Patentability in International Appln. No. PCT/CN2017/103405, dated Apr. 2, 2019, 14 pages (with English Translation).
PCT International Preliminary Report on Patentability in International Appln. No. PCT/CN2018/075427, dated Oct. 22, 2019, 11 pages (with English Translation).
PCT International Preliminary Report on Patentability in International Appln. No. PCT/CN2018/078597, dated Oct. 22, 2019, 16 pages (with English Translation).
PCT International Search Report and Written Opinion in International Appln. No. PCT/CN2017/101062, dated Dec. 8, 2017, 29 pages (with English Translation).
PCT International Search Report and Written Opinion in International Appln. No. PCT/CN2017/101064, dated Dec. 11, 2017, 16 pages (with English Translation).
PCT International Search Report and Written Opinion in International Appln. No. PCT/CN2017/101066, dated Dec. 29, 2017, 19 pages (with English Translation).
PCT International Search Report and Written Opinion in International Appln. No. PCT/CN2017/103405, dated Jan. 4, 2018, 22 pages (with English Translation).
PCT International Search Report and Written Opinion in International Appln. No. PCT/CN2018/075427, dated Apr. 12, 2018, 17 pages (with English Translation).
PCT International Search Report and Written Opinion in International Appln. No. PCT/CN2018/078597, dated Apr. 27, 2018, 24 pages (with English Translation).
Soda et al., "Increased Polyamine Intake Inhibits Age-Associated Alteration in Global DNA Methylation and 1,2-Dimethylhydrazine-Induced Tumorigenesis," PLOS ONE, 2013, 8(5):e64357, 7 pages.
CA Office Action in Canadian Appln. No. 3057206, dated Mar. 31, 2021, 4 pages.

(56) References Cited

OTHER PUBLICATIONS

CA Office Action in Canadian Appln. No. 3057206, dated Oct. 23, 2020, 6 pages.
CA Office Action in Canadian Appln. No. 3064486, dated Mar. 12, 2021, 4 pages.
EP Office Action in European Appln. No. 18787222.1, dated Mar. 2, 2021, 6 pages.
EP Search Report in European Appln. No. 18787222.1, dated Sep. 18, 2020, 9 pages.
EP Search Report in European Appln. No. 18788316.0, dated Dec. 15, 2020, 8 pages.
Hopkinsmedicine.org [online], "Invasive Mammary Carcinoma (IMC)," available on or before Jun. 21, 2021, [Retrieved on Jun. 21, 2021], retrieved from: URL<https://www.hopkinsmedicine.org/breast_center/breast_cancers_other_conditions/invasive_mammary_carcinoma.html>, 2 pages.
KR Office Action in Korean Appln. No. 20197028417, dated Jun. 28, 2021, 10 pages (with English Translation).
Kuo et al., "A systems analysis of the chemosensitivity of breast cancer cells to the polyamine analogue PG-11047," BMC Medicine, BioMed Central, Dec. 2009, 7:77, doi: 10.1186/1741-7015-7-77.
Schmutzler et al., "Innovative strategies for the treatment of thyroid cancer," European Journal of Endocrinology, 2000, 143:15-24.
Sikora, "Cancer drug development in the post-genomic age," Current Science, Sep. 2001, 81(5):549-554.
Zhao et al., "The purinosome, a multi-protein complex involved in the de novo biosynthesis of purines in humans," Chem. Commun., 2013, 49:4444-4452.
Zips et al., "New Anticancer Agents: In Vitro and In Vivo Evaluation," In Vivo, 2005, 16:1-8.
Expasy.org [Online], "Cellosaurus MDA-MB-468 (CVCL 0419)," entry creation Apr. 4, 2012, [Retrieved on Oct. 23, 2021], retrieved from: URL<https://www.expasy.org/cellosaurus/CVCL_0419>, 9 pages.
Hahm, "The Effect of Protein Kinase C Modulation with Bryostatin 1 on Paclitaxel-Induced Growth Inhibition and Apoptosis in Human Breast Cancer," Award No. DAMD17-97-1-7338, Prepared for U.S. Army Medical Research and Material Command Fort Detrick. Maryland 21702-5012, Jan. 2000, 73 pages.
KR Office Action in Korean Appln. No. 20197028417, dated Aug. 30, 2021, 7 pages (with English Translation).
McCloskey et al., "Polyamine analogue induction of programmed cell death in human lung tumor cells," Clinical Cancer Research, 1996, 2(3):441-446.
Office Action in Chinese Appln. No. 201880019008.9, dated Mar. 9, 2022, 11 pages (with English translation).
Bachrach et al., "Polyamines: New Cues in Cellular Signal Transduction," News Physiol Sci., Jun. 2001, 16:106-9.
Search Report in Chinese Appln. No. 201880031224, dated Apr. 27, 2022, 1 page.
Tian, "Study on the Relationship between Autophagy and Viability Decrease of Hela Cells Induced by Spermidine," Thesis, China Master's Theses Full-text Database, Apr. 2013, 4 pages (with Machine English Abstract).
Casero et al., "Recent Advances in the Development of Polyamine Analogues as Antitumor Agents," J. Med. Chem., Aug. 2009, 52:4551-4573.
EP Office Action in European Appln. No. 17854846.7, dated Jul. 6, 2022, 4 pages.
Ha et al., "Structural Specificity of Polyamines and Polyamine Analogues in the Protection of DNA from Strand Breaks Induced by Reactive Oxygen Species," Biochem. Biophys. Res. Commun., Mar. 1998, 244(1):298-303.
Igarashi et al., "Spermine-like functions of N1, N12-bis(ethyl)spermine: stimulation of protein synthesis and cell growth and inhibition of gastric ulceration," Biochem. Biophys. Res. Commun., Oct. 1990, 172(2):715-20.
Seiler, "Pharmacological aspects of cytotoxic polyamine analogs and derivatives for cancer therapy," Pharmacol. Ther., Jul. 2005, 107(1):99-119.
Office Action in Chinese Appln. No. 201880031224.5, dated May 7, 2022, 11 pages (with English Translation).

* cited by examiner

METHODS OF TREATING OR ALLEVIATING ADENYLOSUCCINATELYASE (ADSL) DEFICIENCY USING SPERMIDINE OR A PHARMACEUTICALLY ACCEPTABLE SALT OF SPERMIDINE

CROSS-REFERENCE TO RELATED PATENT APPLICATIONS

This application is a U.S. National Phase Application under 35 U.S.C. § of International Patent Application No. PCT/CN2017/103408, filed Sep. 26, 2017, and claims the priority of Chinese Application No. 201610865163.5, filed Sep. 29, 2016, which is incorporated by reference as if expressly set forth in its entirety herein.

FIELD OF THE INVENTION

The present disclosure relates to compounds which can weaken the activity of SAICAR synthetase, and the use thereof.

BACKGROUND OF THE INVENTION

Anabolism of purine is one kind of prevalent and important biological metabolism in organisms. Its metabolic products, AMP and GMP, provide not only starting materials for biosynthesis of DNA and RNA in the organisms, but also purine bases which are necessary for synthesis of many key coenzymes (NAD, NADP, FAD and CoA), signal molecules (e.g., cAMP) and an important energy molecule ATP in the body. It is thus evident that the anabolism of purine lies in the core position of the whole metabolic network. Purine synthesis includes two synthetic pathways, i.e. de novo purine synthesis and salvage pathway.

Adenylosuccinatelyase deficiency (ADSL deficiency) is one metabolic disease which causes deletion or disorder in de novo adenine synthesis and purine nucleotide metabolic pathway. This disease is primarily caused by the mutation or deletion of adenylosuccinatelyase in patients, which results in the substrate SAICAR of this enzyme is unduly accumulated in cells and cannot be eliminated in time [Jaeken J, Van den Berghe G (1984). An infantile autistic syndrome characterized by the presence of succinylpurines in body fluids. Lancet 8411:1058-1061]. In 1984, Jaeken and Van den Berghe first detected the accumulation of this metabolite in body fluids of several patients with bradykinesia and autism. The patients with adenylosuccinatelyase deficiency usually develop symptoms such as severe dysplasia, bradykinesia, dull-looking, epilepsy, autism and the like [Spiegel, E. K., Colman, R. F., and Patterson, D. (2006). Adenylosuccinatelyase deficiency. Mol Genet Metab 89, 19-31. Clamadieu, C., Cottin, X., Rousselle, C., and Claris, O. (2008). Adenylosuccinatelyase deficiency: an unusual cause of neonatal seizure. Arch Pediatr 15, 135-138. Castro, M., Perez-Cerda, C., Merinero, B., Garcia, M. J., Bemar, J., Gil Nagel, A., Torres, J., Bermudez. M., Garavito, P., Marie. S., et al. (2002). Screening for adenylosuccinatelyase deficiency: clinical, biochemical and molecular findings in four patients. Neuropediatrics 33, 186-189. Jurecka, A., Zikanova, M., Tylki-Szymanska, A., Krijt, J., Bogdanska, A., Gradowska, W., Mullerova, K., Sykut-Cegielska, J., Kmoch. S., and Pronicka, E. (2008b). Clinical, biochemical and molecular findings in seven Polish patients with adenylosuccinatelyase deficiency. Mol Genet Metab 94, 435-4421.

ADSL deficiency has 3 types of continuous main phenotypes: neonatal lethal type, severe (type I) and mild-to-moderate (type II). It was clinically found that patients may have different phenotypes even they come from the same family. The onset of the disease generally occurs from birth to infancy. The reported cases include lethal neonatal encephalopathy (manifested as hypokinesia, intractable epilepsy, respiratory disturbance), and moderate mental deficiency. All the patients have mental deficiency, and most of the patients have different types of epilepsy, and about one third of the patients have autism characteristics (unable to make eye contact, sensitive to sound and light, repetitive behaviors, agitation, temper tantrum, self-injury and self-mutilation). Other unusual clinical manifestations include psychomotor delay, overactivity, language disorder, hypotonia, muscular atrophy and spasm. Patients with severe ADSL deficiency usually have microcephaly. It has been reported that prenatal clinical manifestations include intrauterine growth retardation, microcephaly, fetal hypokinesia and absent of fetal heart rate variability.

In the metabolic pathway of adenine de novo synthesis, adenylosuccinatelyase (hereinafter referred to as ADSL enzyme) mainly participates in the catalytic cracking of SAICAR to form AICAR and in the reaction for generating AMP from S-AMP [Spiegel, E. K., Colman, R. F. and Patterson, D. (2006). Adenylosuccinatelyase deficiency. Mol Genet Metab 89, 19-31. Clamadieu. C., Cottin, X., Rousselle. C., and Claris. 0. (2008). Adenylosuccinatelyase deficiency: an unusual cause of neonatal seizure. Arch Pediatr 15, 135-138. Castro. M., Perez-Cerda, C., Merinero, B., Garcia. M. J., Bemar. J., Gil Nagel, A., Torres. J., Bermudez. M., Garavito. P., Marie. S., et al. (2002). Screening for adenylosuccinatelyase deficiency: clinical. biochemical and molecular findings in four patients, Neuropediatrics 33, 186-189.]. In the patients with adenylosuccinatelyase deficiency, the harmful metabolite SAICAR cannot be eliminated in time due to the mutation or deletion of the ADSL enzyme, which usually makes the patients develop severe neurological and physiological symptoms, such as epilepsy, encephalodysplasia, bradykinesia and the like [Ciardo, F., Salerno. C., and Curatolo, P. (2001). Neurologic aspects of adenylosuccinatelyase deficiency. J Child Neurol 16, 301-308. Gitiaux, C., Ceballos-Picot. I., Marie. S., Valayannopoulos, V., Rio, M., Verrieres, S., Benoist. J. F., Vincent, M. F., Desguerre, I., and Bahi-Buisson, N. (2009). Misleading behavioural phenotype with adenylosuccinatelyase deficiency. Eur J Hum Genet 17, 133-136. Mierzewska. H., Schmidt-Sidor, B., Jurkiewicz, E., Bogdanska, A., Kusmierska. K., and Stepien, T. (2009). Severe encephalopathy with brain atrophy and hypomyelination due to adenylosuccinatelyase deficiency—MRI, clinical, biochemical and neuropathological findings of Polish patients. Folia Neuropathol 47. 314-3201. A large amount of intermediate metabolites SAICAr, which is a product of the dephosphorylation of SAICAR, and S-Ado, which is a product of the dephosphorylation of S-AMP, are usually accumulated in the cerebrospinal- and body fluids of the patients [Spiegel, E. K., Colman, R. F., and Patterson, D. (2006). Adenylosuccinatelyase deficiency. Mol Genet Metab 89, 19-31. Mierzewska, H., Schmidt-Sidor, B., Jurkiewicz, E., Bogdanska, A., Kusmierska. K., and Stepien, T. (2009). Severe encephalopathy with brain atrophy and hypomyelination due to adenylosuccinatelyase deficiency—MRI, clinical, biochemical and neuropathological findings of Polish patients. Folia Neuropathol 47, 314-320.]. Van den Berghe et al. found that the ratio of S-do to SAICAr in the body fluids has certain correlation with the disease severity of the patients [Van den Bergh F, Vincent M F. Jaeken J, Van den Berghe G. (1993). Residual adenylosuccinase activities in fibroblasts of adenylosuccinase-deficient children: parallel deficiency with adenylosuccinate and succinyl-AICAR in profoundly retarded patients and non-parallel deficiency in a mildly retarded girl, J. Inherit. Metab. Dis. 16(2) 415-424.]. Until now, there is no clinically effective therapeutic regimens which can cure ADSL deficiency.

Phosphoribosylaminoimidazolesuccinocarboxamide synthetase/phosphoribosylaminoimidazole carboxylase, i.e. PAICS, is an important bifunctional enzyme in the purine de novo synthesis pathway. It has the functions of SAICAR synthetase (4-(N-succinylcarboxamide)-5-aminoimidazole ribonucleotidesynthetase, SAICARs) and AIR carboxylase (5-aminoimidazole ribonucleotidecarboxylase, AIRc), can catalyze the sixth and seventh steps of the reaction of purine de novo anabolism, in which one key reaction process is shown as follows:

Preceding researches performed by the inventors show that the accumulation of SAICAR and SAICAr can be effectively reduced by interfering with the function of PAICS protein (gene), thereby achieving the goal of treating or improving ADSL deficiency. However, no compound has been reported to have such effect at present.

SUMMARY OF THE INVENTION

An objective of the present disclosure is to provide compounds interfering with SAICAR synthetase activity, and the use thereof.

The inventor, on the basis of existing data relating to protein and small molecule structures, performs calculation and analysis using software, and find that compounds with DrugBank IDs DB03639, DB01821, DB04700, DB02927, DB02267, DB04633, DB04207, DB03433, DB03003, DB01910, DB01813, DB02011, DB03327, DB02075, DB02077, DB01815, DB01974, DB04323, DB03927, DB03582, DB02537, DB01634, DB04153, DB04649, DB04778, DB02824, DB04701, DB01657, DB02941, DB04684, DB02492, DB03427, DB03686, DB04762, DB03602, DB03566, DB04808, DB04341, DB01895, DB03624, DB04434, and DB04602 can effectively interfere with PAICS activity, reduce SAICAR synthesis, and ultimately reduce SAICAr accumulation, thereby achieving the goal of treating or improving ADSL deficiency.

The pharmaceutically acceptable derivatives of the above compounds may have the same parent core structures as the compounds per se, and can produce molecules having the same or similar activity as the original compounds through reactions such as hydrolysis and the like in vivo, resulting in the same or similar therapeutic efficacy.

The pharmaceutically acceptable derivatives of the compounds may particularly refer to simple derivatives thereof, and especially refer to one of lower ester, lower ether, lower alkyl substituent, pharmaceutical salt and lower amide thereof, i.e., derivatives obtained by condensation of carboxylic acid, alcohol, amine having 1 to 6, preferably 2 to 6, or 2 to 4 carbon atom(s) with the parent compounds.

The pharmaceutically acceptable pharmaceutical salts of the compounds can be synthesized from the parent compounds by conventional chemical methods, such as the method described in *Pharmaceutical Salts: Properties, Selection and Use*, P Heinrich Stahl (Editor), Camille G Wermuth (Editor), ISBN: 3-90639-026-8, Hardcover, 388 pages, August 2002. In general, such salts can be prepared by reacting free alkali of the compound with an acid in water, organic solvent or a mixed solution of both. Usually, a non-aqueous media can be used, such as ethyl ether, ethyl acetate, ethanol, isopropanol or acetonitrile.

An acid addition salt may be prepared with various acids (inorganic acids and organic acids). The examples of the acid addition salt may include salts prepared from an acid which may be selected from a group consisting of acetic acid, 2,2-dichloroacetic acid, adipic acid, alginic acid, ascorbic acid (such as L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (such as D-glucuronic acid), glutamic acid (such as L-glutamic acid), α-ketoglutaric acid, glycolic acid, hippuric acid, hydrobromic acid, hydrochloric acid, hydroiodic acid, hydroxyethylsulfonic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid and pentanoic acid, as well as acyl-amino acid and cation exchange resin.

By combined utilization of at least two of the above compounds, it is expected to obtain better effect of treating or improving ADSL deficiency.

BRIEF DESCRIPTION OF THE DRAWINGS

FIG. 3 shows the alignment result of different types of SAICAR synthetase protein sequences.

DETAILED DESCRIPTION OF THE EMBODIMENTS

Figure 1:
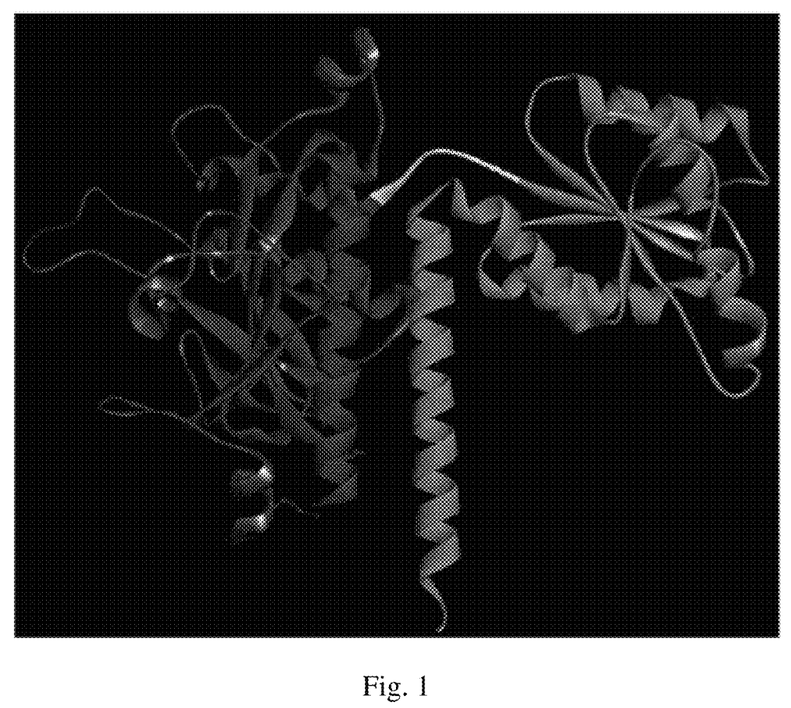
FIG. 1 shows a 3D solid ribbon structure diagram of PAICS.

There are 425 amino acid residues in full length of the human PAICS protein sequence, in which a fragment of 2-260 AA is a SAICAR synthetase domain, and a fragment of 267-425AA is an AIR carboxylase domain, these two domains are linked by a 6-peptide (KSESQC). Furthermore, GLN159-GLN183 α-helix in the SAICAR synthetase domain interacts with ASN395-ASN424 α-helix in the AIR carboxylase domain, and tightly bind together, as shown in FIG. 1.

A protein structure data bank (RCSB) collects the crystal structure data of SAICAR synthetases of different origins, which include *Saccharomyces cerevisiae* (1A48, 2CNQ, 2CNV, 2CNU, 1OBD, 1OBG), *Pyrococcushorikoshii* OT3 (3U54, 3U55), *Escherichia coli* (2GQR, 2GQS), Methanocaldococcusjannaschii (2YZL, 2Z02), *Streptococcus pneumonia* (4FGR, 4FE2), *Mycobacterium abscessus* ATCC 19977/DSM 44196 (3R9R), *Thermotoga maritime* (1KUT), *Clostridium perfringens* (3NUA), *Ehrlichiachaffeensis* (3KRE), *Geobacilluskaustophilus* (2YWV) as well as PAICS crystal structure data *Homo sapiens* (2H31) and *Bombyxmori* (4JA0). Wherein, there are complexes 2GQS, 2CNQ and 4FE2 which contain the structure of CAIR, and complexes 2CNV, 2CNU and 4FE2 which contain the structure of ASP.

Figure 2:
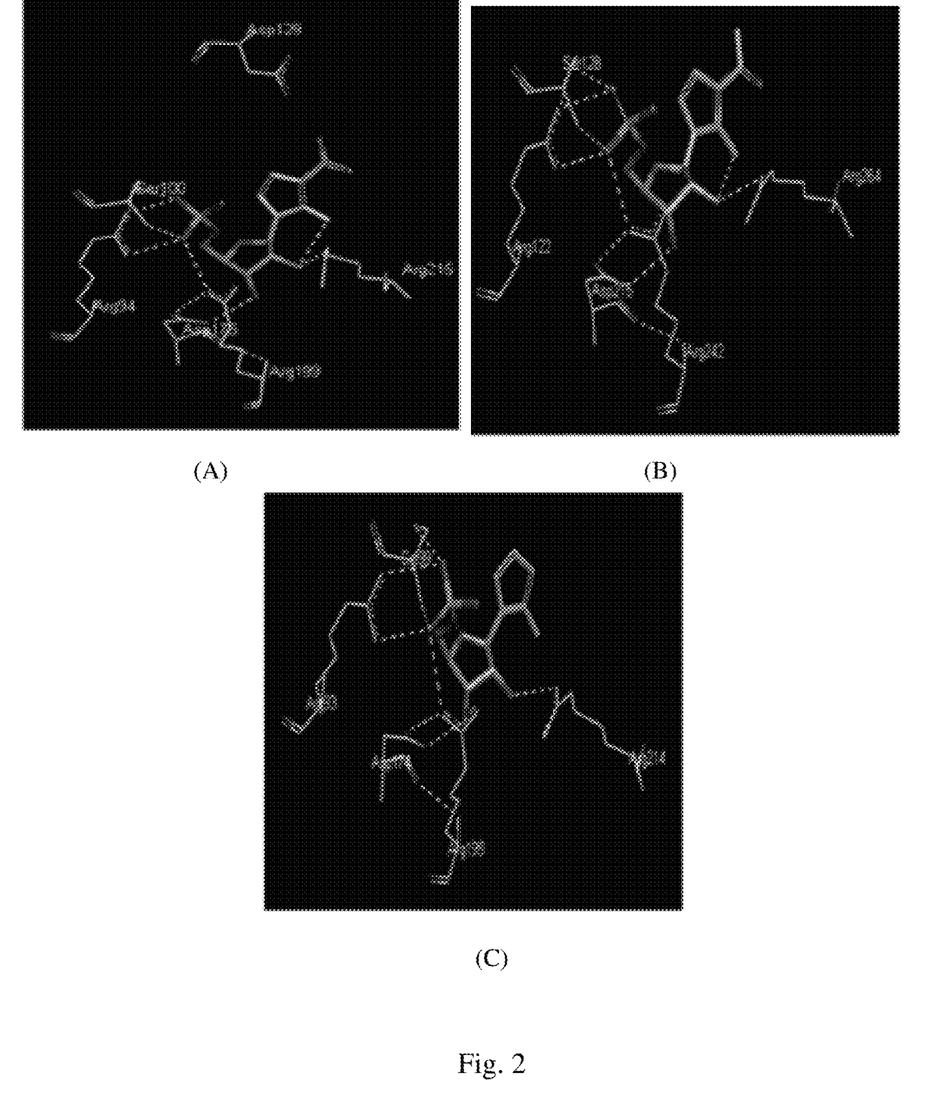
FIG. 2 shows diagrams indicating the interaction of CAIR and SAICAR synthetase in the crystal structure, in which A: PDB access ID 2GQS; B: PDB access ID 2CNQ; and C: PDB access ID 4FE2.

As shown in FIG. 2, the residues within CAIR 3A in 2CNQ are Arg122, Ser128, ASP215, Arg242 and Arg264; the residues within CAIR 3A in 2GQS are Arg94, Ser100, ASP129, ASP175, Arg199 and Arg215; the residues within CAIR 3A in 4FE2 are Arg93, Ser99, ASP174, Arg199, and Arg214. With reference to the alignment result of the SAICAR protein sequences of different species (FIG. 3), it can be seen that the binding sequences of SAICAR synthetases of different species with CAIR exhibits high-level conservative, and CAIR is primarily fixed by hydrogen bonds.

On the basis of the above results, the crystal structure conformations in SAICAR synthetases of *Saccharomyces cerevisiae* (PDB: 2CNQ) and *Escherichia coli* (PDB: 2GQS) are used as receptor structures for calculating and screening, since there is no conformation which can bind CAIR in human PAICS crystal structure, and no catalytic conformation formed in the catalytic region, and the results obtained by calculation are not reliable. 4661 of small molecule drugs in the DrugBank (www.drugbank.ca) are calculated and screened by using the ligand fit module of Discovery studio. The conformations are ordered according to dock scores, and then the first 500 conformations are selected. After eliminating the repetitions, key screening results are obtained. In addition, the inhibition ratios of the compounds against SAICAR accumulation are confirmed by biochemical enzyme activity experiments and cell biology experiments, as shown in Table 1.

TABLE 1

Calculating-Screening Results and SAICAR Inhibition Ratio Results
SAICAR synthetase of *Escherichia coli*

| No. | DrugBank ID | Common name | Dock Score | Inhibition ratios against SAICAR accumulation |
|---|---|---|---|---|
| 1 | DB03639 | 1-Guanidinium-7-Aminoheptane | 365.651 | 79.185% |
| 2 | DB01821 | L-N(Omega)-Nitroarginine-2,4-L-Diaminobutyric Amide | 279.201 | 57.11% |
| 3 | DB04700 | GLUTATHIONE SULFINATE | 276.972 | 9.98% |
| 4 | DB02927 | Mixed Carbamic Phosphoric Acid Anhydride of 7,8-Diaminononanic acid | 272.952 | 22.8% |
| 5 | DB02267 | Argininosuccinate | 268.699 | 86.81% |
| 6 | DB04633 | N-ethyl-N[3-(propylamino)propyl]propane-1,3-diamine | 262.124 | 12.798% |
| 7 | DB04207 | N-(5-Amino-5-Carboxypentyl)-Glutamic Acid | 261.457 | 65.69% |
| 8 | DB03433 | {[(3-Hydroxy-2-Methyl-5-Phosphonooxymethyl-Pyridin-4-ylmethyl)-Amino]-2-Methyl-Propyl}-Phosphonic Acid | 261.442 | 53.38% |
| 9 | DB03003 | Glutathione Sulfonic acid | 261.371 | 38% |
| 10 | DB01910 | Adenosyl-Ornithine | 260.798 | 29.69% |
| 11 | DB01813 | Pyridoxyl-Glutamic Acid-5'-Monophosphate | 260.557 | 40.9% |
| 12 | DB02011 | N-(phosphonoacetyl)-L-Ornithine | 260.026 | 41.85% |
| 13 | DB03327 | {1-[(3-Hydroxy-Methyl-5-Phosphonooxy-Methyl-Pyridin-4-Ylmethyl)-Amino]-Ethyl}-Phosphonic acid | 259.637 | 13.25% |
| 14 | DB02075 | (1s)-1-(9-Deazahypoxanthin-9-yl)-1,4-Di Deoxy-1,4-Imino-D-Ribitol-5-Phosphate | 258.501 | 28.5% |
| 15 | DB02077 | L-N(Omega)-Nitroarginine-(4r)-Amino-L-Proline Amide | 258.008 | 71.8% |

TABLE 1-continued

Calculating-Screening Results and SAICAR Inhibition Ratio Results
SAICAR synthetase of *Escherichia coli*

| No. | DrugBank ID | Common name | Dock Score | Inhibition ratios against SAICAR accumulation |
|---|---|---|---|---|
| 16 | DB01815 | Nz-(Dicarboxymethyl)Lysine | 257.918 | 22.68% |
| 17 | DB01974 | 2-Amino-3-[5-(Amino-Carboxy-Methyl)-2,3-Dihydro-Isoxazol-3-Ylsulfanyl]-Propionic Acid | 253.882 | 66.711% |
| 18 | DB04323 | 2-Amino-3-(Cystein-S-Yl)-Isoxazolidin-5-Yl-Acetic acid | 252.875 | 56.68% |
| 19 | DB03927 | Glycyl-L-Alpha-Amino-Epsilon-Pimelyl-D-Alanine | 252.376 | 29.859% |
| 20 | DB03582 | N-2-Succinylornithine | 252.353 | 19.97% |
| 21 | DB02537 | 2-Hydroxy-5-({1-[(4-Methylphenoxy)Methyl]-3-Oxoprop-1-Enyl}Amino)-L-Tyrosin | 248.151 | 71.1% |
| 22 | DB01634 | 2-Oxy-4-Hydroxy-5-(2-Hydrazinopyridine)Phenylalanine | 246.192 | 23.7% |
| 23 | DB04153 | S-Hydroxymethyl Glutathione | 245.035 | 58% |
| 24 | DB04649 | TETRAHEDRAL INTERMEDIATE OF BLASTICIDIN S | 244.418 | 20.09% |
| 25 | DB04778 | SC45647 | 243.957 | 11.29% |
| 26 | DB02824 | N-Pyridoxyl-Glycine-5-Monophosphate | 243.609 | 77.97% |
| 27 | DB04701 | S-METHYL-GLUTATHIONE | 243.574 | 40.1% |
| 28 | DB01657 | 2-Amino-3-[4-Hydroxy-6-Oxo-3-(2-Phenyl-Cyclopropylimino)-Cyclohexa-1,4-Dienyl]-Propionic acid | 243.414 | 22.9% |
| 29 | DB02941 | 3-(1-Aminoethyl)Nonanedioic Acid | 243.33 | 69.8% |
| 30 | DB04684 | BIS(HEXAMETHYLENE)TRIAMINE | 242.609 | 9.3% |
| 31 | DB02492 | Ghavamiol | 242.096 | 17.4% |
| 32 | DB03427 | Delta-(L-Alpha-Aminoadipoyl)-L-Cysteinyl-D-Vinylglycine | 241.85 | 13.3% |
| 33 | D1303686 | S-(P-Nitrobenzyl)Glutathione | 240.981 | 63.83% |
| 34 | DB04762 | N-PYRIDOXYL-D-GLUTAMIC ACID-5'-MONOPHOSPHATE | 240.901 | 27.7% |
| 35 | DB03602 | S-Benzyl-Glutathione | 240.844 | 36.5% |
| 36 | DB03566 | Spermidine | 239.222 | 68.98% |
| 37 | D1304808 | Neamine | 239.011 | 37.11% |
| 38 | DB04341 | S-(3-Iodobenzyl)Glutathione | 235.101 | 9.9% |
| 39 | DB01895 | Aspartyl-Adenosine-5'-Monophosphate | 233.296 | 22.918% |
| 40 | DB03624 | 7-(Carboxyamino)-8-Amino-Nonanoic Acid | 232.98 | 51.9% |
| 41 | DB04434 | Naphthyridine Inhibitor | 232.928 | 22.98% |
| 42 | DB04602 | PUROMYCIN AMINONUCLEOSIDE-5'-MONOPHOSPHATE | 249.924 | 12.9% |

Computer screening results show that all the compounds listed in the above table can effectively interact with PAICS, influence SAICAR synthesis, and thus reduce the accumulation of the toxic metabolite. Therefore, it is expected that these compounds can be developed as drug or health-care products for treating ADSL deficiency.

The pharmaceutically acceptable derivatives of the above compounds have the same parent core structures as the compounds per se, and can produce molecules having the same or similar activity as the original compounds through reactions such as hydrolysis and the like in vivo, resulting in the same or similar therapeutic efficacy.

The pharmaceutically acceptable derivatives of the compounds may particularly refer to simple derivatives thereof, and especially refer to one of lower ester, lower ether, lower alkyl substituent, pharmaceutical salt and lower amide thereof, i.e., derivatives obtained by condensation of carboxylic acid, alcohol, amine having 1 to 6, preferably 2 to 6, or 2 to 4 carbon atom(s) with the parent compounds.

The pharmaceutically acceptable pharmaceutical salts of the compounds can be synthesized from the parent compound by conventional chemical methods, such as the method described in *Pharmaceutical Salts: Properties, Selection and Use*, P Heinrich Stahl (Editor), Camille G Wermuth (Editor), ISBN: 3-90639-026-8, Hardcover, 388 pages, August 2002. In general, such salts can be prepared by reacting free alkali of the compounds with an acid in water, organic solvent or a mixed solution of both; generally, a non-aqueous media can be used, such as ethyl ether, ethyl acetate, ethanol, isopropanol or acetonitrile.

Acid addition salts can be prepared with various acids (inorganic acids and organic acids). The examples of the acid addition salts may include salts prepared from an acid which may be selected from a group consisting of acetic acid, 2,2-dichloroacetic acid, adipic acid, alginic acid, ascorbic acid (such as L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (such as D-glucuronic acid), glutamic acid (such as L-glutamic acid), α-ketoglutaric acid, glycolic acid, hippuric acid, hydrobromic acid, hydrochloric acid, hydroiodic acid, hydroxyethylsulfonic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene- 2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid and pentanoic acid, as well as acyl-amino acid and cation exchange resin.

Combined utilization of the drugs can improve therapeutic effect, and reduce toxic and side effects to a certain extent. Preferably, 2, 3, 4, 5 or more compounds or derivatives thereof can be simultaneously used as the active ingredients for treating ADSL deficiency.

What is claimed is:

1. A method for treating or alleviating a disease, comprising administering a therapeutically effective amount of a compound or a pharmaceutically acceptable salt thereof to a patient in need thereof,
wherein the compound is spermidine, and the disease is adenylosuccinatelyase (ADSL) deficiency.

2. The method according to claim 1, wherein the administering comprises administering spermidine to the patient.

3. The method according to claim 1, wherein the administering comprises administering a pharmaceutically acceptable salt of spermidine to the patient.

4. The method according to claim 3, wherein the pharmaceutically acceptable salt is prepared from spermidine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, hydroxyethylsulfonic acid, (+)-L-lactic acid, (+)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acyl-amino acid.

5. The method according to claim 1, wherein ADSL deficiency is neonatal lethal type ADSL deficiency, type I ADSL deficiency, or type II ADSL deficiency.

* * * * *

UNITED STATES PATENT AND TRADEMARK OFFICE
CERTIFICATE OF CORRECTION

| | | |
|---|---|---|
| PATENT NO. | : 11,766,412 B2 | Page 1 of 1 |
| APPLICATION NO. | : 16/334256 | |
| DATED | : September 26, 2023 | |
| INVENTOR(S) | : Wuguang Pan and Wei Zhu | |

It is certified that error appears in the above-identified patent and that said Letters Patent is hereby corrected as shown below:

In the Specification

Column 1, Line 11, before "of" insert -- 371 --.

Signed and Sealed this
Twenty-eighth Day of November, 2023

Katherine Kelly Vidal
*Director of the United States Patent and Trademark Office*